(12) United States Patent
Doehling et al.

(10) Patent No.: US 7,749,283 B2
(45) Date of Patent: Jul. 6, 2010

(54) COLORANT WITH NACREOUS LUSTER FOR KERATIN FIBERS

(75) Inventors: Annelie Doehling, Muenster (DE); Helga Kreher, Muenster (DE); Dirk Lauscher, Darmstadt (DE)

(73) Assignee: Wella AG, Darmstadt (DE)

( * ) Notice: Subject to any disclaimer, the term of this patent is extended or adjusted under 35 U.S.C. 154(b) by 864 days.

(21) Appl. No.: 10/585,377

(22) PCT Filed: Oct. 20, 2004

(86) PCT No.: PCT/EP2004/011854

§ 371 (c)(1),
(2), (4) Date: Jul. 5, 2006

(87) PCT Pub. No.: WO2005/074871

PCT Pub. Date: Aug. 18, 2005

(65) Prior Publication Data

US 2009/0172896 A1    Jul. 9, 2009

(30) Foreign Application Priority Data

Feb. 5, 2004 (DE) .................. 10 2004 005 769

(51) Int. Cl.
*A61Q 5/10* (2006.01)
(52) U.S. Cl. ............... 8/405; 8/406; 8/435; 8/580; 8/597; 8/604; 8/611
(58) Field of Classification Search ............... 8/405, 8/406, 435, 580, 597, 604, 611
See application file for complete search history.

(56) References Cited

U.S. PATENT DOCUMENTS

| 4,381,919 | A * | 5/1983 | Jacquet et al. ............... 8/405 |
| 5,525,123 | A | 6/1996 | Lorenz et al. |
| 6,528,045 | B1 | 3/2003 | Golinski et al. |
| 2002/0046431 | A1 * | 4/2002 | Laurent et al. ............... 8/405 |
| 2003/0074747 | A1 | 4/2003 | Vuarier et al. |

FOREIGN PATENT DOCUMENTS

| DE | 35 06 543 | 8/1986 |
| DE | 38 34 142 | 4/1990 |
| DE | 43 31 136 | 8/1994 |
| DE | 195 44 655 | 6/1997 |
| DE | 198 25 133 | 2/2000 |
| DE | 198 47 224 | 4/2000 |
| EP | 1 293 192 | 3/2003 |
| EP | 1 428 509 | 6/2004 |
| WO | 2004/019895 | 3/2004 |

OTHER PUBLICATIONS

E. Sagarin: "Cosmetics Scinece and Technology", Interscience Publishers Inc, NY, 1957 pp. 503-507 (in English).
H. Janistyn: "Handbuch Der Kosmetika Und . . . " Band 3, 1973, pp. 388-397.
K. Schrader: Grundlagen Und Rezepturen Der Kosmetika:, 2 Auflage, 1989, pp. 782-815.
Fiedler—Lexicon Der Hilfsstoffe, Band 1, 5. Auflage 2002, pp. 105-113.

* cited by examiner

*Primary Examiner*—Eisa B Elhilo
(74) *Attorney, Agent, or Firm*—Michael J. Striker

(57) ABSTRACT

The object of the present application is a dye carrier composition containing oxidative and/or non-oxidative dyes as well as
(a) 6.1 to 25 weight percent of at least one fatty alcohol with 14 to 20 carbon atoms,
(b) 1 to 20 weight percent of at least one fatty acid alkanolamide and
(c) 1 to 15 weight percent of at least one fatty alcohol alkoxylate and/or fatty acid alkoxylate,
the weight ratio of fatty alcohol (a) to fatty acid alkanolamide (b) being equal to 4:1 to 1:3 and at the same time the weight ratio of fatty alcohol (a) to alkoxylate (c) being equal to 5:1 to 1:2. Another object is the use of the afore-said combination of components (a) to (c) to produce a nacreous luster effect in dye carrier compositions and colorants for keratin fibers.

6 Claims, No Drawings

COLORANT WITH NACREOUS LUSTER FOR KERATIN FIBERS

CROSS-REFERENCE TO RELATED APPLICATIONS:

This is the US National Stage of PCT/EP04/11854, filed on 20 Oct. 2004, and claims the priority under 35 U.S.C. 119(a)-(d) to German Patent Application No. 10 2004 005 769.9, filed 05 Feb. 2004.

BACKGROUND OF THE INVENTION

1. Field of the Invention

The invention relates to agents with a nacreous luster for coloring keratin fibers, particularly human hair, containing direct and/or oxidation dyes and a special combination of fatty alcohols, fatty alkanolamides and fatty alcohol alkoxylates and/or fatty acid alkoxylates as well as to the use of the afore-said combination for producing a stable nacreous luster in hair colorants.

2. Description of Related Art

Coloring preparations are usually in the form of aqueous—preferably thickened—solutions or emulsions and besides dyes contain, for example, fatty alcohols and/or other oil components, emulsifiers, surfactants and optionally alcohols. Oxidation dyes as a rule consist of two components, namely (i) the dye carrier composition containing the dyes and (ii) the oxidant preparation, which are mixed with one another just before use and are then applied to the hair to be colored. If the coloring preparations are in the form of emulsions, they are as a rule stable creams, but to obtain a nacreous luster it is necessary to add to them a special nacreous luster-imparting agent.

From DE-A 38 34 142 are known creamy hair colorants containing a multiplicity of raw materials including fatty alcohols and fatty alkanolamides as well as anionic and nonionic surfactants. These colorants, however, do not have a nacreous luster.

BRIEF SUMMARY OF THE INVENTION

The purpose was therefore to develop a coloring composition which by the selection of the raw materials alone and without the addition of a nacreous luster-imparting agent would have a stable nacreous character which would be retained also after the mixing with the oxidant preparation.

We have now found that this objective can be reached in eminent fashion by use of a combination of a fatty alcohol, a fatty alkanolamide and a fatty alcohol alkoxylate and/or fatty acid alkoxylate.

DETAILED DESCRIPTION OF THE INVENTION

The object of the present invention is therefore a dye carrier composition containing oxidation and/or non-oxidation ("direct") dyes, characterized in that it contains a combination of (a) 6.1 to 25 weight percent of at least one fatty alcohol with 14 to 20 carbon atoms, (b) 1 to 20 weight percent of at least one fatty alkanolamide and (c) 1 to 15 weight percent of at least one fatty alcohol alkoxylate and/or fatty acid alkoxylate, the weight ratio of fatty alcohol (a) to fatty alkanolamide (b) being equal to 4:1 to 1:3 and at the same time the weight ratio of fatty alcohol (a) to alkoxylate (c) being equal to 5:1 to 1:2.

The preferred weight ratio of fatty alcohol (a) to alkanolamide (b) in the dye carrier composition to obtain a beautiful nacreous luster is from 3:1 to 2:1 and particularly from 2.5:1 to 1:1. The weight ratio of fatty alcohol (a) to alkoxylate (c) in this case is preferably from 4:1 to 1:1.5 and particularly from 3:1 to 1:1.

Long-chain fatty alcohols (a) with 14 to 20 carbon atoms suitable according to the invention are, for example, cetyl alcohol, stearyl alcohol, myristyl alcohol, isooctyl alcohol or isotridecyl alcohol. In the dye carrier composition, the fatty alcohols can be used alone or in combination with one another.

Alkanolamides (b) suitable according to the invention are, in particular, the N-acyl derivatives of monoethanolamine, for example coconut fatty acid monoethanolamide, or the N-acyl derivatives of diethanolamine as well as the monoethanolamine or diethanolamine esters. The alkanolamides can be used alone or in combination with one another.

Alkoxylates (c) suitable according to the invention are fatty alcohol polyalkylene glycol ethers and/or fatty acid polyalkylene glycol esters with 8 to 30 carbon atoms in the fatty alcohol group or fatty acid group and 2 to 300 alkylene glycol units in the polyalkylene glycol group. Preferred are polyalkylene glycol alkoxylates of ethylene glycol or propylene glycol as well as combined polyethylene glycol alkoxylates/polypropylene glycol alkoxylates. Particularly preferred are fatty alcohol alkoxylates, for example the polyethylene glycol ethers of stearyl alcohol, for example Steareth-10, Ceteareth-25 or Steareth-20. The fatty alcohol alkoxylates and fatty acid alkoxylates can be used alone or in combination with one another.

Component (a) is used in the dye carrier composition of the invention in a total amount from 6.1 to 25 weight percent, preferably in a total amount from 7 to 20 weight percent and particularly in a total amount from 8 to 15 weight percent.

Component (b) is used in the dye carrier composition of the invention in a total amount from 1 to 20 weight percent, preferably in a total amount from 2 to 15 weight percent and particularly in a total amount from 4 to 10 weight percent.

Component (c) is used in the dye carrier composition of the invention in a total amount from 1 to 15 weight percent, preferably in a total amount from 2 to 10 weight percent and particularly in a total amount from 3 to 6 weight percent.

The dye carrier composition of the invention preferably contains oxidation dye precursors from which the color is produced by action of an oxidant, for example hydrogen peroxide or an adduct thereof, or in the presence of atmospheric oxygen.

Suitable oxidation dye precursors are, for example the following developers and couplers and self-coupling substances:

(i) Developers: 1,4-diaminobenzene (p-phenylenediamine), 1,4-diamino-2-methylbenzene (p-toluylenediamine), 1,4-diamino-2,6-dimethylbenzene, 1,4-diamino-3,5-diethylbenzene, 1,4-diamino-2,5-dimethylbenzene, 1,4-diamino-2,3-dimethylbenzene, 2-chloro-1,4-diaminobenzene, 1,4-diamino-2-(thiophen-2-yl)benzene, 1,4-diamino-2-(thiophen-3-yl)benzene, 1,4-diamino-2-(pyridin-3-yl)-benzene, 2,5-diaminobiphenyl, 1,4-diamino-2-methoxymethylbenzene, 1,4-diamino-2-aminomethylbenzene, 1,4-diamino-2-hydroxymethylbenzene, 1,4-diamino-2-(2-hydroxyethoxy)benzene, 2-[(2-acetylamino)ethoxy]-1,4-diaminobenzene, 4-phenylaminoaniline, 4-dimethylaminoaniline, 4-diethylaminoaniline, 4-dipropylaminoaniline, 4-[ethyl(2-hydroxyethyl)amino]aniline, 4-[di(2-hydroxyethyl)amino]aniline, 4-[di(2-hydroxyethyl)amino-2-methylaniline, 4-[(2-methoxyethyl)amino]aniline, 4-[(3-hydroxypropyl)amino]aniline, 4-[(2,3-dihydroxypropyl)amino]aniline, 1,4-diamino-2-(2-hydroxyethyl)benzene, 1,4-diamino-2-(1-methylethyl)benzene, 1,3-bis[(4-aminophenyl)(2-hydroxyethyl)amino]-2-propanol, 1,4-bis[(4-aminophenyl)amino]butane, 1,8-bis(2,5-diaminophenoxy)-3,6-dioxa-octane, 4-aminophenol, 4-amino-3-methylphenol, 4-amino-3-(hydroxymethyl)phenol, 4-amino-3-fluorophenol, 4-methylaminophenol, 4-amino-2-(aminomethyl)phenol, 4-amino-2-(hydroxymethyl)phenol, 4-amino-2-fluorophenol, 4-amino-2-[(2-hydroxyethyl)amino]methylphenol, 4-amino-2-methylphenol, 4-amino-2-(methoxyethyl)phenol, 4-amino-2-(2-hydroxyethyl)phenol, 5-amino-salicylic acid, 2,5-diaminopyridine, 2,4,5,6-tetraaminopyrimidine, 2,5,6-triamino-4-(1H)-pyrimidone, 4,5-diamino-1-(2-hydroxyethyl)-1H-pyrazole, 4,5-diamino-1-(1-methylethyl)-1H-pyrazole, 4,5-diamino-1-[(4-methylphenyl)methyl]-1H-pyrazole, 1-[(4-chlorophenyl)methyl]-4,5-diamino-1H-pyrazole, 4,5-diamino-1-methyl-1H-pyrazole, 2-aminophenol, 2-amino-6-methylphenol and 2-amino-5-methylphenol, alone or in admixture with one another.

(ii) Couplers: N-(3-Dimethylaminophenyl)urea, 2,6-diaminopyridine, 2-amino-4-[(2-hydroxyethyl)amino]anisole, 2,4-diamino-1-fluoro-5-methylbenzene, 2,4-diamino-1-methoxy-5-methylbenzene, 2,4-diamino-1-ethoxy-5-methylbenzene, 2,4-diamino-1-(2-hydroxyethoxy)-5-methylbenzene, 2,4-di[(2-hydroxyethyl)amino-1,5-dimethoxybenzene, 2,3-diamino-6-methoxypyridine, 3-amino-6-methoxy-2-(methylamino)pyridine, 2,6-diamino-3,5-dimethoxypyridine, 3,5-diamino-2,6-dimethoxy-pyridine, 1,3-diaminobenzene, 2,4-diamino-1-(2-hydroxyethoxy)benzene, 1,3-diamino-4-(2,3-dihydroxypropoxy)benzene, 2,4-diamino-1,5-di(2-hydroxyethoxy)benzene, 1-(2-aminoethoxy)-2,4-diaminobenzene, 2-amino-1-(2-hydroxyethoxy)-4-methylaminobenzene, 2,4-diaminophenoxyacetic acid, 3-[di(2-hydroxyethyl)amino]aniline, 4-amino-2-di[(2-hydroxyethyl)amino]-1-ethoxybenzene, 5-methyl-2-(1-methylethyl)phenol, 3-[(2-hydroxyethyl)amino]aniline, 3-[(2-aminoethyl)amino]aniline, 1,3-di(2,4-diaminophenoxy)propane, di(2,4-diaminophenoxy)methane, 1,3-diamino-2,4-dimethoxy-benzene, 2,6-bis(2-hydroxyethyl)aminotoluene, 4-hydroxyindole, 3-dimethylaminophenol, 3-dieth-ylaminophenol, 5-amino-2-methylphenol, 5-amino-4-fluoro-2-methylphenol, 5-amino-4-methoxy-2-methylphenol, 5-amino-4-ethoxy-2-methylphenol, 3-amino-2,4-dichlorophenol, 5-amino-2,4-dichlo-rophenol, 3-amino-2-methylphenol, 3-amino-2-chloro-6-methylphenol, 3-aminophenol, 2-[(3-hydroxyphenyl)amino]acetamide, 5-[(2-hydroxyethyl)amino]-4-methoxy-2-methylphenol, 5[(2-hydroxyethyl)amino]-2-methylphenol, 3[(2-hydroxyethyl)amino]phenol, 3-[(2-methoxyethyl)amino]phenol, 5-amino-2-ethylphenol, 5-amino-2-methoxyphenol, 2-(4-amino-2-hydroxyphenoxy)ethanol, 5-[(3-hydroxypropyl)amino]-2-methylphenol, 3-[(2,3-dihydroxypropyl)amino]-2-methylphenol, 3-[(2-hydroxyethyl)amino]-2-methylphenol, 2-amino-3-hydroxypyridine, 5-amino-4-chloro-2-methylphenol, 1-naphthol, 2-methyl-1-naphthol, 1,5-dihydroxynaphthalene, 1,7-dihydroxynaphthalene, 2,3-dihydroxynaphthalene, 2,7-dihydroxynaphthalene, 2-methyl-1-naphthol acetate, 1,3-dihydroxybenzene, 1-chloro-2,4-dihydroxybenzene, 2-chloro-1,3-dihydroxybenzene, 1,2-dichloro-3,5-dihydroxy-4-methylbenzene, 1,5-dichloro-2,4-dihydroxybenzene, 1,3-dihydroxy-2-methylbenzene, 3,4-methylenedioxyphenol, 3,4-methylenedioxyaniline, 5-[(2-hydroxyethyl)amino]-1,3-benzodioxol, 6-bromo-1-hydroxy-3,4-methylenedioxybenzene, 3,4-diaminobenzoic acid, 3,4-dihydro-6-hydroxy-1,4(2H)-benzoxazine, 6-amino-3,4-dihydro-1,4(2H)-benzoxazine, 3-methyl-1-phenyl-5-pyrazolone, 5,6-dihydroxyindole, 5,6-dihydroxyindoline, 5-hydroxyindole, 6-hydroxyindole, 7-hydroxyindole and 2,3-indolinedione, alone or in admixture with one another.

(iii) Self-coupling substances: 2-amino-5-methylphenol, 2-amino-6-methylphenol, 2-amino-5-ethoxyphenol or 2-propylamino-5-aminopyridine.

The total amount of oxidation dye precursors contained in the dye carrier composition of the invention is about 0.01 to 12 weight percent and particularly about 0.2 to 8 weight percent.

Moreover, to achieve certain color nuances the colorant can also contain common natural and/or synthetic direct dyes, for example vegetable dyes such as henna or indigo, triphenylmethane dyes, aromatic nitro dyes, azo dyes, quinone dyes or cationic or anionic dyes.

Suitable synthetic dyes are, for example: 1,4-bis[(2-hydroxyethyl)amino]-2-nitrobenzene, 1-(2-hydroxyethyl)amino-2-nitro-4-[di(2-hydroxyethyl)amino]benzene (HC Blue No. 2), 1-amino-3-meth-yl-4-[(2-hydroxyethyl)amino]-6-nitrobenzene (HC Violet No. 1), 4-[ethyl-(2-hydroxyethyl)amino]-1-[(2-hydroxyethyl)amino]-2-nitrobenzene hydrochloride (HC Blue No. 12), 4-[di(2-hydroxyeth-yl)amino]-1-[(2-methoxyethyl)amino]-2-nitrobenzene (HC Blue No. 11), 1-[(2,3-dihydroxypropyl)-amino]-4-[methyl-(2-hydroxyethyl)amino]-2-nitrobenzene (HC Blue No. 10), 1-[(2,3-dihydroxy-propyl)amino]-4-[ethyl-(2-hydroxyethyl)amino]-2-nitrobenzene hydrochloride (HC Blue No. 9), 1-(3-hydroxypropylamino)-4-[di(2-hydroxyethyl)amino]-2-nitrobenzene (HC Violet No. 2), 1-methylami-no-4-[methyl-(2,3-dihydroxypropyl)amino]-2-nitrobenzene (HC Blue No. 6), 2-[(4-amino-2-nitro-phenyl)amino]-5-dimethylaminobenzoic acid (HC Blue No. 13), 1-amino-4-[(2-hydroxyethyl)-amino]-2-nitrobenzene (HC Red No. 7), 2-amino-4,6-dinitrophenol, 4-amino-2-nitrodiphenylamine (HC Red No. 1), 1-amino-4-[di(2-hydroxyethyl)amino]-2-nitrobenzene hydrochloride (HC Red No. 13), 1-amino-5-chloro-4-[(2-hydroxyethyl)amino]-2-nitrobenzene, 4-amino-1-[(2-hydroxyethyl)ami-no]-2-nitrobenzene (HC Red No. 3), 4-amino-3-nitrophenol, 4-[(2-hydroxyethyl)amino]-3-nitro-phenol, 1-[(2-aminoethyl)amino]-4-(2-hydroxyethoxy)-2-nitrobenzene (HC Orange No. 2), 4-(2,3-dihydroxypropoxy)-1-[(2-hydroxyethyl)amino]-2-nitrobenzene (HC Orange No. 3), 1-amino-5-chlo-ro-4-[(2,3-dihydroxypropyl)amino]-2-nitrobenzene (HC Red No. 10), 5-chloro-1,4-[di(2,3-dihydroxypropyl)amino]-2-nitrobenzene (HC Red No. 11), 2-[(2-hydroxyethyl)amino]-4,6-dinitrophe-nol, 4-ethylamino-3-nitrobenzoic acid, 2-[(4-amino-2-nitrophenyl)amino]benzoic acid, 2-chloro-6-ethylamino-4-nitrophenol, 2-amino-6-chloro-4-nitrophenol, 4-[(3-hydroxypropyl)amino]-3-nitrophe-nol, 2,5-diamino-6-nitropyridine, 1,2,3,4-tetrahydro-6-nitroquinoxaline, 7-amino-3,4-dihydro-6-nitro-2H-1,4-benzoxazine, (HC Red. No. 14), 1-amino-2-[(2-hydroxyethyl)amino]-5-nitrobenzene (HC Yellow No. 5), 1-(2-hydroxyethoxy)-2-[(2-hydroxyethyl)amino]-5-nitrobenzene (HC Yellow No. 4), 1-[(2-hydroxyethyl)amino]-2-nitrobenzene (HC Yellow No. 2), 2-[(2-hydroxyethyl)amino]-1-meth-oxy-5-nitrobenzene, 2-amino-3-nitrophenol, 1-(2-hydroxyethoxy)-3-methylamino-4-nitrobenzene, 2,3-(dihydroxypropoxy)-3-methylamino-4-nitrobenzene, 2-[(2-hydroxyethyl)amino]-5-nitrophenol (HC Yellow No. 11), 3-[(2-aminoethyl)amino]-1-methoxy-4-nitrobenzene hydrochloride (HC Yellow No. 9), 1-[(2-ureidoethyl)amino]-4-nitrobenzene, 4-[(2,3-dihydroxypropyl)amino]-3-nitro-1-trifluoromethylbenzene (HC Yellow No. CI6), 1-chloro-2,4-bis[(2-hydroxyethyl)amino]-5-nitrobenzene (HC Yellow No. 10), 4-[(2-hydroxyethyl)amino]-3-nitro-1-methylbenzene, 1-chloro-4-[(2-hydroxyethyl)amino]-3-nitrobenzene (HC Yellow No. 12), 4-[(2-hydroxyethyl)amino]-3-nitro-1-trifluoromethylbenzene (HC Yellow No. 13), 4-[(2-hydroxyethyl)amino]-3-nitrobenzonitrile (HC Yellow No. 14), 4-[(2-hydroxyethyl)amino]-3-nitrobenzamide (HC Yellow No. 15), 1,4-di[(2,3-dihydroxypropyl)amino]-9,10-anthraquinone, 1-[(2-hydroxyethyl)amino]-4-methylamino-9,10-anthraquinone (CI 61505, Disperse Blue No. 3), 2-[(2-aminoethyl)amino]-9,10-anthraquinone (HC Orange No. 5), 1-hydroxy-4-[(4-methyl-2-sulfophenyl)amino]-9,10-anthraquinone, 1-[(3-aminopropyl)amino]-4-methylamino-9,10-anthraquinone (HC Blue No. 8), 1-[(3-aminopropyl)amino]-9,10-anthraquinone (HC Red No. 8), 1,4-diamino-2-methoxy-9,10-anthraquinone (CI 62015, Disperse Red No. 11, Solvent Violet No. 26), 1,4-dihydroxy-5,8-bis[2-hydroxyethyl)amino]-9,10-anthraquinone (CI 62500, Disperse Blue No. 7, Solvent Blue No. 69), 9-(dimethylamino)benzo[a]-phenoxazin-7-ium chloride (Cl 51175; Basic Blue No. 6), di[4-(diethylamino)phenyl][4-(ethylamino)naphthyl]carbenium chloride (CI 42595; Basic Blue No. 7), 3,7-di(dimethylamino)phenothiazin-5-ium chloride (CI 52015; Basic Blue No. 9), di[4-(dimethylamino)phenyl][4-(phenylamino)naphthyl]carbenium chloride (CI 44045; Basic Blue No. 26), 2-{[4-(ethyl(2-hydroxyethyl)amino)phenyl]azo}-6-methoxy-3-methylbenzothiazolium methylsulfate (CI 11154; Basic Blue No. 41), 8-amino-2-bromo-5-hydroxy-4-imino-6-{[3-(trimethylammonio)phenyl]amino}-1(4H-naphthalenone chloride (CI 56059; Basic Blue No. 99), bis[4-(dimethylamino)phenyl][4-(methylamino)phenyl]carbenium chloride (CI 42535; Basic Violet No. 1), tris[4-(dimethylamino)phenyl]carbenium chloride (CI 42555; Basic Violet No. 3), 2-[3,6-(diethylamino)dibenzopyranium-9-yl]benzoyl chloride (CI 45170; Basic Violet No. 10), di(4-aminophenyl)(4-amino-3-methylphenyl)carbenium chloride (CI 42510, Basic Violet No. 14), 1,3-bis[(2,4-diamino-5-methylphenyl)azo]-3-methylbenzene (CI 21010; Basic Brown No. 4), 1-[(4-aminophenyl)azo]-7-(trimethylammonio)-2-naphthol chloride (CI 12250; Basic Brown No. 16), 1-[(4-amino-2-nitrophenyl)azo]-7-(trimethylammonio-2-naphthol chloride (Basic Brown No. 17), 1-[(4-amino-3-nitrophenyl)azo]-7-(trimethylammonio)-2-naphthol chloride (CI 12251; Basic Brown No. 17 [sic]), 3,7-diamino-2,8-dimethyl-5-phenylphenazinium chloride (CI 50240; Basic Red No. 2), 1,4-dimethyl-5-{[(4-(dimethylamino)phenyl]azo}-1,2,4-triazolium chloride (CI 11055; Basic Red No. 22), 2-hydroxy-1-[(2-methoxyphenyl)azo]-7-(trimethylammonio)naphthalene chloride (Cl 12245; Basic Red No. 76), 2-{2-[(2,4-dimethoxyphenyl)amino]ethenyl}-1,3,3-trimethyl-3H-indol-1-ium chloride (CI 48055; Basic Yellow No. 11), 3-methyl-1-phenyl-4-{[3-(trimethylammonio)phenyl]azo}pyrazol-5-one chloride (CI 12719; Basic Yellow No. 57), bis[4-(diethylamino)phenyl]phenylcarbenium hydrogen sulfate (1:1) (CI 42040; Basic Green No. 1), 1-[di(2-hydroxyethyl)amino]-3-methyl-4-[(4-nitrophenyl)azo]benzene (CI 11210; Disperse Red No. 17), 4-[(4-aminophenyl)azo]-1-[di(2-hydroxyethyl)amino]-3-methylbenzene (HC Yellow No. 7), 2,6-diamino-3-[(pyridin-3-yl)azo]pyridine, 6-hydroxy-5-[(4-sulfophenyl)azo]-2-naphthalenesulfonic acid disodium salt (CI 15985; Food Yellow No. 3; FD&C Yellow No. 6), 2,4-dinitro-1-naphthol-7-sulfonic acid disodium salt (CI 10316; Acid Yellow No. 1; Food Yellow No. 1), 2-(indan-1,3-dion-2-yl)quinoline-x,x-sulfonic acid (mixture of mono- and disulfonic acid) (CI 47005; D&C Yellow No. 10; Food Yellow No. 13; Acid Yellow No. 3), 5-hydroxy-1-(4-sulfophenyl)-4-[(4-sulfophenyl)azo]pyrazole-3-carboxylic acid trisodium salt (CI 19140; Food Yellow No. 4; Acid Yellow No. 23), 9-(2-carboxyphenyl)-6-hydroxy-3H-xanthen-3-one (CI 45350; Acid Yellow No. 73; D&C Yellow No. 8), 5-[(2,4-dinitrophenyl)amino]-2-phenylaminobenzenesulfonic acid sodium salt (CI 10385; Acid Orange No. 3), 4-[(2,4-dihydroxyphenyl)azo]benzenesulfonic acid monosodium salt (CI 14270; Acid Orange No. 6), 4-[(2-hydroxynaphth-1-yl)azo]benzenesulfonic acid sodium salt (CI 15510; Acid Orange No. 7), 4-[(2,4-dihydroxy-3-[(2,4-dimethylphenyl)azo]phenyl)azo]benzenesulfonic acid sodium salt (CI 20170; Acid Orange No. 24), 4-hydroxy-3-[(4-sulfonaphth-1-yl)azo]-1-naphthalenesulfonic acid disodium salt (CI 14720; Acid Red No. 14), 6-hydroxy-5-[(4-sulfonaphth-1-yl)azo]-2,4-naphthalenedisulfonic acid trisodium salt (CI 16255; Ponceau 4R; Acid Red No. 18), 3-hydroxy-4-[(4-sulfonaphth-1-yl)azo]-2,7-naphthalenedisulfonic acid trisodium salt (CI 16185; Acid Red No. 27), 8-amino-1-hydroxy-2-(phenylazo)-3,6-naphthalenedisulfonic acid disodium salt (Cl 17200; Acid Red No. 33), 5-(acetylamino)-4-hydroxy-3-[(2-methylphenyl)azo]-2,7-naphthalenedisulfonic acid disodium salt (CI 18065; Acid Red No. 35), 2-(3-hydroxy-2,4,5,7-tetraiododibenzopyran-6-on-9-yl)benzoic acid disodium salt (CI 45430; Acid Red No. 51), N-[6-(diethylamino)-9-(2,4-disulfophenyl)-3H-xanthen-3-ylidene]-N-ethylethanammonium hydroxide, inner salt, sodium salt (CI 45100; Acid Red No. 52), 8-{[4-(phenylazo)phenyl]azo}-7-naphthol-1,3-disulfonic acid disodium salt (CI 27290; Acid Red No. 73), 2',4',5',7'-tetrabromo-3',6'-dihydroxyspiro[isobenzofuran-1(3H),9'-[9H]-xanthen]-3-one disodium salt (CI 45380; Acid Red No. 87), 2',4',5',7'-tetrabromo-4,5,6,7-tetrachloro-3',6'-dihydroxyspiro[isobenzofuran-1(3H),9'-[9H]-xanthen]-3-one disodium salt (CI 45410; Acid Red No. 92), 3',6'-dihydroxy-4',5'-diiodispiro[isobenzofuran-1(3H),9'(9H)xanthen]-3-one disodium salt (CI 45425; Acid Red No. 95), {{2-sulfophenyldi{4-ethyl-(4-sulfophenyl)methylyl]amino}phenyl}}carbenium disodium salt betaine (CI 42090; Acid Blue No. 9; FD&C Blue No. 1), 1,4-bis[(2-sulfo-4-methylphenyl)amino]-9,10-anthraquinone disodium salt (CI 61570; Acid Green No. 25), bis[4-(dimethylamino)phenyl]-3,7-disulfo-2-hydroxynaphth-1-yl)car-benium inner salt, monosodium salt (CI 44090; Food Green No. 4; Acid Green No. 50), bis[4-(diethylamino)phenyl][2,4-disulfophenyl)carbenium inner salt, sodium salt (2:1) (CI 42045; Food Blue No. 3; Acid Blue No. 1), bis[4-(diethylamino)phenyl](5-hydroxy-2,4-disulfo-phenyl)carbenium inner salt, calcium salt (2:1) (CI 42051; Acid Blue No. 3), 1-amino-4-(cyclo-hexylamino)-9,10-anthraquinone-2-sulfonic acid sodium salt (CI 62045; Acid Blue No. 62), 2-(1,3-dihydro-3-keto-5-sulfo-2H-indol-2-ylidene)-2,3-dihydro-3-keto-1H-indole-5-sulfonic acid disodium salt (CI 73015; Acid Blue No. 74), 9-(2-carboxyphenyl)-3-[(2-methylphenyl)amino]-6-[(2-methyl-4-sulfophenyl)amino]-xanthylium inner salt, monosodium salt (CI 45190; Acid Violet No. 9), 1-hy-droxy-4-[(4-methyl-2-sulfophenyl)amino]-9,10-anthraquinone sodium salt (CI 60730; D&C Violet No. 2; Acid Violet No. 43), bis{3-nitro-4-[(4-phenylamino)-3-sulfophenylamino]phenyl}sulfone (CI 10410; Acid Brown No. 13), 5-amino-4-hydroxy-6-[(4-nitrophenyl)azo]-3-(phenylazo)-2,7-naph-thalenedisulfonic acid disodium salt (CI 20470; Acid Black No. 1), 3-hydroxy-4-[(2-hydroxynaphth-1-yl)azo]-7-nitro-1-naphthalene-sulfonic acid chromium complex (3:2) (CI 15711; Acid Black No. 52), 3-[(2,4-dimethyl-5-sulfophenyl)azo]-4-hydroxy-1-naphthalenesulfonic acid disodium salt (CI 14700; Food Red No. 1; FD&C Red No. 4), 4-(acetylamino)-5-hydroxy-6-[(7- sulfo-4-[(4-sulfo-phenyl)azo]naphth-1-yl)azo]-1,7-naphthalenedisulfonic acid tetrasodium salt (Cl 28440; Food Black No. 1) and 3-hydroxy-4-(3-methyl-5-keto-1-phenyl-4,5-dihydro-1H-pyrazol-4-ylazo)-naphthalene-1-sulfonic acid sodium salt, chromium complex (Acid Red No. 195), alone or in com-bination with one another The total amount of direct dyes in the dye carrier composition of the invention is about 0.01 to 7 weight percent and preferably about 0.2 to 4 weight percent.

Other common dyes known to be used for hair coloring and which can be contained in the colorant of the invention are described in, among other publications, E. Sagarin, "Cosmetics, Science and Technology", Interscience Publishers Inc., New York (1957), pages 503 ff, and in H. Janistyn, "Handbuch der Kosmetika und Riechstoffe" [Handbook of Cosmetics and Fragrances], vol. 3 (1973), pages 368 ff and K. Schrader "Grundlagen und Rezepturen der Kosmetika" [Fundamentals and Formulations of Cosmetics], 2nd edition, (1989), pages 782 to 815, to which we hereby specifically refer.

Although the dye carrier composition is particularly well suited for oxidation colorants, nonoxidative colorants based on the afore-said direct dyes can, of course, also be prepared with the dye carrier composition of the invention.

To further improve the rinsability after use, the colorant of the invention can also contain other surfactants besides the compounds of component (c). Preferably, nonionic and amphoteric surfactants and combinations thereof are contained in the colorant of the invention, because they confer outstanding compatibility with other ionogenic—both anionic and cationic—additives. Moreover, the use of nonionic and amphoteric surfactants and combinations thereof brings about a further enhancement of the hair-care effect.

Amphoteric surfactants suitable according to the invention are acylethyldiamines and derivatives thereof, N-alkylamino acids or iminodicarboxylic acids and particularly betaines, for example cocamidopropylbetaine. Nonionic surfactants suitable according to the invention are polyethylene glycols, polypropylene glycols, ethylene oxide/propylene oxide block polymers, alkylphenolethoxylates, alkylpolyglucosides, ethoxylated alkanolamides, glycol esters and glycerol esters and the alkoxylates thereof, sorbitan esters and the alkoxylates thereof, alkyl carbohydrate esters (sugar esters), alkyl carbohydrate ethers (sugar ethers), ethoxylated pentaerythritol esters and alkoxylated polysiloxanes.

A detailed description of these nonionic or amphoteric surfactants can be found in the publication "FIEDLER-Lexikon der Hilfsfoffe" [FIEDLER-Encyclopedia of Auxiliary Substances], vol. 1, 5th edition (2002), pages 105 to 113, to which we hereby specifically refer.

The colorant of the invention can contain these additional surfactants in a total amount from 0.1 to 10 wt. % and preferably from 0.5 to 6 weight percent.

Furthermore, the dye carrier composition of the invention can contain antioxidants, for example ascorbic acid, thioglycolic acid or sodium sulfite, as well as complexing agents for heavy metals, for example an ethylenediaminetetraacete or nitriloacetic acid, in an amount of up to about 1.5 weight percent. Perfume oils can be contained in the dye carrier composition of the invention in an amount of up to about 1.5 weight percent. Naturally, the afore-described dye carrier composition can optionally also contain other additives commonly used in hair colorants, for example thickeners such as, for example, the homopolymers of acrylic acid, vegetable gums, derivatives of cellulose and starch, algal polysaccharides, amphiphilic associative thickeners, moreover preservatives, antioxidants, for example sodium sulfite, thioglycolic acid and ascorbic acid or mixtures thereof, complexing agents, solvents such as water, the lower aliphatic alcohols, for example aliphatic alcohols with 1 to 4 carbon atoms such as ethanol and isopropanol, or glycols such as glycerol and 1,2-propylene glycol, other wetting agents or emulsifiers, moreover softeners, vaseline, silicone oils, paraffin oil, polysorbates and fatty acids as well as hair-care agents such as cationic polymers or resins, lanolin derivatives, cholesterol, vitamins, pantothenic acid or betaine. The said constituents are used in amounts normally employed for such purposes, for example the wetting agents and emulsifiers at a concentration of 0.1 to 30 weight percent and the hair-care agents at a concentration of 0.1 to 5.0 weight percent.

The colorant of the invention is preferably free of cationic and anionic surfactants and emulsifiers as well as of ethylene glycol distearate and monomeric quaternary ammonium compounds.

For nonoxidative colorants based on direct dyes, the pH of the dye carrier composition of the invention is in the range from about 5 to 10 and preferably from 6 to 9, whereas for oxidative colorants based on oxidation dye precursors the pH is in the range from about 6 to 12 and preferably from 9 to 11, the pH of the ready-to-use oxidation hair colorant (namely the mixture of the dye carrier composition of the invention and the oxidant) being about 5.5 to 10.5 and preferably 6 to 10.

Depending on the composition and the desired pH, the pH is preferably adjusted with ammonia, an amino acid or an organic amine, for example a glucamine, aminomethylpropanol, monoethanolamine or triethanolamine, an inorganic base, for example sodium hydroxide, potassium hydroxide, sodium carbonate, sodium metasilicate or calcium hydroxide, or with an organic or inorganic acid, for example lactic acid, citric acid, acetic acid or phosphoric acid.

The dye carrier composition of the invention is preferably packaged in the form of an aqueous or aqueous-alcoholic preparation, for example as a thickened solution, emulsion, cream or gel.

For oxidative coloring, the afore-described dye carrier composition is mixed with an oxidant just before use, and an amount of the ready-to-use colorant sufficient for the coloring, as a rule about 60 to 200 grams, is applied to the fibers.

If the dye carrier composition of the invention contains no oxidation dye presursors or contains oxidation dye precursors that are readily oxidized by atmospheric oxygen, it can be applied to the keratin fibers directly without previous mixing with an oxidant.

Suitable oxidants for developing the coloration are mainly hydrogen peroxide or the addition compounds thereof to urea, melamine or sodium borate in the form of a 1- to 12-percent, preferably 1.5 to 6 percent aqueous solution. The mixing ratio of dye carrier composition to oxidant depends on the concentration of the oxidant and as a rule is about 5:1 to 1:3 and preferably 1:1, the oxidant being contained in the ready-to-use preparation preferably in an amount from about 0.5 to 8 weight percent and particularly from 1 to 4 weight percent.

The ready-to-use colorant is allowed to act on the keratin fibers (for example on human hair) at 15 to 50° C. for about 10 to 45 minutes and preferably for about 15 to 30 minutes after which the fibers are rinsed with water. Optionally, following this rinsing the fibers are washed with a shampoo and possibly post-rinsed with a weak organic acid, for example tartaric acid. The keratin fibers are then dried.

The dye carrier composition of the invention has a uniform consistency and produces a highly cosmetic nacreous effect. A colorant prepared with the dye carrier composition of the invention meets the requirements in terms of adhesion, application performance and viscosity adjustment in outstanding manner and through the nacreous character provides a highly cosmetic appearance.

Another object of the present application is the use of a combination of
(a) at least one fatty alcohol with 14 to 20 carbon atoms,
(b) at least one fatty alkanolamide and
(c) at least one fatty alcohol alkoxylate and/or fatty acid alkoxylate, the weight ratio of fatty alcohol (a) to alkanolamide (b) in the dye carrier composition being equal to 4:1 to 1:3, the ratio of fatty alcohol (a) to alkoxylate (c) at the same time being 5:1 to 1:2, for producing a nacreous luster in dye carrier compositions and colorants for keratin fibers, particularly human hair.

Particularly preferred is the use of a combination of
(a) 6.1 to 25 weight percent, particularly 7 to 20 weight percent and more particularly 8 to 15 weight percent of at least one fatty alcohol with 14 to 20 carbon atoms,
(b) 1 to 20 weight percent, particularly 2 to 15 weight percent and more particularly 4 to 10 weight percent of at least one fatty alkanolamide and
(c) 1 to 15 weight percent, particularly 2 to 10 weight percent and more particularly 3 to 6 weight percent of at least one fatty alcohol alkoxylate and/or fatty acid alkoxylate, the weight ratio of fatty alcohol (a) to alkanolamide (b) in the dye carrier composition being equal to 3:1 to 1:2 and particularly to 2.5:1 to 1:1 and the weight ratio of fatty alcohol (a) to alkoxylate (c) at the same time being equal to 4:1 to 1:1.5 and particularly 3:1 to 1:1.

To further improve the rinsability following use, other surfactants may be added to the aforesaid combination besides the compounds of component (c). Preferably, nonionic and amphoteric surfactants and combinations thereof are added, because they confer excellent compatibility with other ionogenic—both anionic and cationic—additives. Moreover, by use of nonionic and amphoteric surfactants and combinations thereof, the hair-care effect can be further enhanced.

The following examples will explain the subject matter of the invention without limiting it to the examples.

EXAMPLES

Example 1

Oxidation Hair Colorant, Creamy

| |
| --- |
| 8.00 g of stearyl alcohol |
| 4.00 g of ceterayl alcohol |
| 1.00 g of propylene glycol |
| 6.00 g of coco fatty acid monoethanolamide (Cocamide MEA) |
| 2.50 g of Ceteareth-25 |
| 2.00 g of Steareth-20 |
| 4.00 g of cocamidopropylbetaine (30% aqueous solution) |
| 1.90 g of 2,5-diaminotoluene sulfate |
| 0.40 g of resorcinol |
| 0.10 g of m-aminophenol |
| 0.12 g of 2-methylresorcinol |
| 0.10 g of α-naphthol |
| 0.10 g of 2-amino-4-hydroxyethylaminoanisol sulfate |
| 0.10 g of HC Yellow No. 13 |
| 0.60 g of 2,4-diaminophenoxyethanol sulfate |
| 4.55 g of ammonia, 25% aqueous solution |
| 0.30 g of disodium ethylenediaminetetraacetate |
| 0.40 g of ascorbic acid |
| 0.50 g of Polyquaternium-11 |
| 2.00 g of alanine |
| to 100.00 g water |

Just before use, 50 g of the foregoing dye carrier composition with a nacreous luster was mixed with 50 g of a 6% aqueous hydrogen peroxide solution. A homogeneous, cosmetically attractive colorant preparation having a nacreous luster was obtained. The mixture thus obtained was then applied to blond hair. After an exposure time of 30 minutes at 40° C., the hair was rinsed with water and dried. The hair had a black color.

Example 2

Creamy Oxidation Hair Colorant

| Component (A): Creamy Dye Carrier Composition |
| --- |
| 14.000 g of cetearyl alcohol |
| 2.500 g of PPG-10-cetyl ether |
| 7.000 g of coco fatty acid monoethanolamide (Cocamide MEA) |
| 3.000 g of Ceteareth-25 |
| 1.000 g of oleic acid |
| 1.500 g of Polysorbate-60 |
| 0.260 g of 2,5-diaminotoluene sulfate |
| 0.140 g of resorcinol |
| 0.005 g of m-aminophenol |
| 0.002 g of amino-4-hydroxyethylaminoanisol sulfate |
| 0.005 g of 2-methylresorcinol |
| 0.010 g of hydroxyethyl-2-nitro-p-toluidine |
| 0.500 g of disodium ethylenediaminetetraacetate |
| 16.000 g of ammonia, 25% aqueous solution |
| 3.000 g of creatine |
| 3.000 g of dimethyldiallylammonium chloride/acrylamide copolymer (Polyquaternium-7) |
| to 100.000 g water |

| Component (B): Hydrogen Peroxide Emulsion |
| --- |
| 10.0 g of cetylstearyl alcohol |
| 1.5 g of cholesterol |
| 4.0 g of sodium lauryl alcohol diethylene glycol ether sulfate, 28% aqueous solution |
| 35.0 g of hydrogen peroxide, 35% aqueous solution |
| 0.3 g of perfume |
| to 100.0 g water |

Just before use, 40 g of dye carrier composition (A) was mixed with 80 g of hydrogen peroxide emulsion (B) which corresponded to an (A):(B) weight ratio of 1:2, and 120 g of this mixture was applied to gray hair. After an exposure time of 20 minutes at room temperature, the hair was rinsed with water and then dried. The hair treated in this manner had a uniform bright-blond color from the hair roots to the hair tips. The colorant with a nacreous luster of the invention was easy to apply and did not run off the hair.

Example 3

Oxidation Hair Colorant, Creamy

| |
| --- |
| 14.00 g of stearyl alcohol |
| 2.50 g of PEG-30 stearate |
| 10.00 g of coco fatty acid monoethanolamide (Cocamide MEA) |
| 3.00 g of Ceteareth-25 |
| 5.00 g of cocamidopropylbetaine (30% aqueous solution) |
| 8.00 g of monoethanolamine |
| 2.30 g of 1-hydroxyethyl-4,5-diaminopyrazol sulfate |
| 1.19 g of 4-amino-m-cresol |
| 0.10 g of HC Red No. 10 |
| 0.20 g of 2-amino-6-chloro-4-nitrophenol |
| 0.50 g of keratin hydrolyzate |

-continued

> 0.50 g of silk protein hydrolyzate
> 0.50 g of Cyclomethicone
> 0.50 g of disodium ethylenediaminetetraacetate
> 0.30 g of ascorbic acid
> 0.10 g of sodium sulfite
> to 100.00 g water Just before use, 50 g of the foregoing dye carrier composition was mixed with 50 g of a 12% aqueous hydrogen peroxide solution. The resulting mixture was then applied to medium-blond natural hair. After an exposure time of 30 minutes at 40° C., the hair was rinsed with water and dried. This gave a uniform, strong orange-red color.

Example 4

Colorant with Direct Dyes

> 2.000 g of cetearyl alcohol
> 8.000 g of stearyl alcohol
> 2.000 g of myristyl alcohol
> 6.000 g of coco fatty acid monoethanolamide (Cocamide MEA)
> 2.000 g of Steareth-20
> 3.000 g of Ceteth-20
> 5.000 g of cocamidopropylhydroxysultaine
> 2.000 g of isopropyl alcohol
> 0.160 g of HC Blue 12
> 0.170 g of HC Yellow 13
> 0.012 g of hydroxyethyl-2-nitrotoluidine
> 0.035 g of HC RED NO. 10 and HC RED NO. 11 (1:1)
> 1.000 g of dimethyldiallylammoniuum chloride/acrylamide copolymer (Polyquaternium-7)
> 0.200 g of cationic cellulose derivative (Polyquaternium-10)
> to 100.000 g water The creamy dye composition with a nacreous luster was applied with gloves to washed and towel-dried natural blond hair and allowed to act for 20 to 25 minutes. Excess dye was washed out with water and shampoo. This gave a beautiful, lustrous, medium-blond shade.

Example 5

Hair Colorant with Direct Dyes

> 12.0 g of stearyl alcohol
> 6.0 g of coco fatty acid diethanolamide (Cocamide DEA)
> 2.5 g of PPG-5-Ceteth-20
> 2.5 g of Ceteareth-25
> 7.0 g of ethanol, aqueous
> 0.1 g of hydroxyethyl-2-nitrotoluidine
> 0.5 g of HC RED NO. 10 and HC RED NO. 11 (1:1)
> 0.2 g of 2-amino-6-chloro-4-nitrophenol -continued > 2.0 g of dimethyldiallylammonium chloride/acrylamide copolymer (Polyquaternium-7)
> 0.5 g of cationic cellulose derivative (Polyquaternium-10)
> to 100.0 g water The creamy dye composition with a nacreous luster was applied with gloves to washed and towel-dried natural blond hair and allowed to act for 20 to 25 minutes. Excess dye was washed out with water and a shampoo. This gave a beautiful, lustrous red-blond shade.

Unless otherwise indicated, all percentages given in the present application are by weight.

The invention claimed is:

1. A lustrous dye carrier composition consisting of:
   at least one oxidative dye precursor and/or at least one direct dye;
   a combination of:
   (a) from 6.1 to 25 weight percent of at least one fatty alcohol with 14 to 20 carbon atoms,
   (b) from 1 to 20 weight percent of at least one fatty alkanolamide, and
   (c) from 1 to 15 weight percent of at least one fatty alcohol alkoxylate and/or fatty acid alkoxylate;
   at least one pH adjusting agent;
   at least one additive ingredient selected from the group of amphoteric surfactants, nonionic surfactants, antioxidants, perfume oils, thickeners, preservatives, complexing agents, solvents, softeners, lanolin derivatives, cholesterol, vitamins, pantothenic acid, and betain;
   wherein:
   a weight ratio of said at least one fatty alcohol to said at least one fatty alkanolamide is from 3:1 to 2:1;
   a weight ratio of said at least one fatty alkanolamide to said alkoxylate is from 5:1 to 1:1.5; and
   a total amount of said at least one oxidative dye precursor, when present, is from 0.01 to 12 percent and a total amount of said at least one direct dye, when present, is from about 0.01 to 7 weight percent.

2. The lustrous dye carrier composition as defined in claim 1, wherein the fatty alcohol (a) is selected from the group consisting of cetyl alcohol, stearyl alcohol, myristyl alcohol, isooctyl alcohol, isotridecyl alcohol and mixtures of these compounds.

3. The lustrous dye carrier composition as defined in claim 1, wherein the alkanolamide (b) is selected from among the N-acyl derivatives of monoethanolamine or diethanolamine and the esters of monoethanolamine and diethanolamine.

4. The lustrous dye carrier composition as defined in claim 1, wherein the alkoxylate (c) is selected from the group consisting of fatty alcohol polyalkylene glycol ethers and fatty acid polyalkylene glycol esters with 8 to 30 carbon atoms in the fatty alcohol group or fatty acid group and with 2 to 300 alkylene glycol units in the polyalkylene glycol group.

5. An agent for oxidative coloring of hair, wherein the agent is obtained by mixing a lustrous dye carrier composition as defined in claim 1 with an oxidant.

6. The agent as defined in claim 5, wherein the oxidant is hydrogen peroxide.

* * * * *